US010314693B2

(12) United States Patent
Braido et al.

(10) Patent No.: US 10,314,693 B2
(45) Date of Patent: Jun. 11, 2019

(54) CUFF STITCHING REINFORCEMENT

(71) Applicant: St. Jude Medical, Cardiology Division, Inc., St. Paul, MN (US)

(72) Inventors: Peter N. Braido, Wyoming, MN (US); Andrea L. McCarthy, Vadnais Heights, MN (US); Kent J. Smith, Shoreview, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 74 days.

(21) Appl. No.: 14/548,723

(22) Filed: Nov. 20, 2014

(65) Prior Publication Data

US 2015/0148893 A1 May 28, 2015

Related U.S. Application Data

(60) Provisional application No. 61/909,496, filed on Nov. 27, 2013.

(51) Int. Cl.
*A61F 2/24* (2006.01)
*D05B 1/12* (2006.01)
*D05B 1/14* (2006.01)

(52) U.S. Cl.
CPC .......... *A61F 2/2409* (2013.01); *A61F 2/2412* (2013.01); *D05B 1/12* (2013.01); *D05B 1/14* (2013.01); *A61F 2/2418* (2013.01); *A61F 2220/0008* (2013.01);
(Continued)

(58) Field of Classification Search
CPC .... A61F 2/2418; A61F 2/2412; A61F 2/2409; A61F 2220/0075; A61F 2/07; A61F 2220/0008; A61F 2/2442; A61F 2/2445; A61F 2/86; A61F 2/856; A61F 2/89
See application file for complete search history.

(56) References Cited

U.S. PATENT DOCUMENTS

| | | | |
|---|---|---|---|
| 3,657,744 A | 4/1972 | Ersek | |
| 4,275,469 A | 6/1981 | Gabbay | |
| 4,423,730 A | 1/1984 | Gabbay | |

(Continued)

FOREIGN PATENT DOCUMENTS

| | | |
|---|---|---|
| DE | 19857887 A1 | 7/2000 |
| DE | 10121210 A1 | 11/2002 |

(Continued)

OTHER PUBLICATIONS

International Search Report and Written Opinion for Application No. PCT/US2014/066524 dated Feb. 5, 2015.

(Continued)

*Primary Examiner* — Ann Schillinger
(74) *Attorney, Agent, or Firm* — Lerner, David, Littenberg, Krumholz & Mentlik, LLP

(57) ABSTRACT

A prosthetic heart valve includes a collapsible and expandable stent having a proximal end, a distal end, an annulus section adjacent the proximal end and an aortic section adjacent the distal end, the stent including a plurality of struts. A cuff may be coupled to the stent so that a flat, bottom edge of the cuff lies adjacent the proximal end of the stent. A pattern of stitches may be circumferentially disposed around the flat bottom edge of the cuff, the pattern of stitches alternating between stitches sewn to the cuff only and stitches sewn to both the cuff and the stent.

13 Claims, 10 Drawing Sheets

(52) U.S. Cl.
CPC .......... *A61F 2220/0075* (2013.01); *A61F 2250/0023* (2013.01); *A61F 2250/0069* (2013.01)

(56) References Cited

U.S. PATENT DOCUMENTS

| | | | |
|---|---|---|---|
| 4,491,986 A | 1/1985 | Gabbay | |
| 4,759,758 A | 7/1988 | Gabbay | |
| 4,878,906 A | 11/1989 | Lindemann et al. | |
| 4,922,905 A | 5/1990 | Strecker | |
| 4,994,077 A | 2/1991 | Dobben | |
| 5,411,552 A | 5/1995 | Andersen et al. | |
| 5,480,423 A | 1/1996 | Ravenscroft et al. | |
| 5,843,167 A | 12/1998 | Dwyer et al. | |
| 5,855,601 A | 1/1999 | Bessler et al. | |
| 5,924,424 A | 7/1999 | Stevens et al. | |
| 5,935,163 A | 8/1999 | Gabbay | |
| 5,961,549 A | 10/1999 | Nguyen et al. | |
| 5,968,068 A | 10/1999 | Dehdashtian et al. | |
| 6,077,297 A | 6/2000 | Robinson et al. | |
| 6,083,257 A | 7/2000 | Taylor et al. | |
| 6,090,140 A | 7/2000 | Gabbay | |
| 6,214,036 B1 | 4/2001 | Letendre et al. | |
| 6,264,691 B1 | 7/2001 | Gabbay | |
| 6,267,783 B1 | 7/2001 | Letendre et al. | |
| 6,306,141 B1 | 10/2001 | Jervis | |
| 6,368,348 B1 | 4/2002 | Gabbay | |
| 6,419,695 B1 | 7/2002 | Gabbay | |
| 6,468,660 B2 | 10/2002 | Ogle et al. | |
| 6,488,702 B1 | 12/2002 | Besselink | |
| 6,517,576 B2 | 2/2003 | Gabbay | |
| 6,533,810 B2 | 3/2003 | Hankh et al. | |
| 6,582,464 B2 | 6/2003 | Gabbay | |
| 6,610,088 B1 | 8/2003 | Gabbay | |
| 6,623,518 B2 | 9/2003 | Thompson et al. | |
| 6,685,625 B2 | 2/2004 | Gabbay | |
| 6,719,789 B2 | 4/2004 | Cox | |
| 6,730,118 B2 | 5/2004 | Spenser et al. | |
| 6,783,556 B1 | 8/2004 | Gabbay | |
| 6,790,230 B2 | 9/2004 | Beyersdorf et al. | |
| 6,814,746 B2 | 11/2004 | Thompson et al. | |
| 6,830,584 B1 | 12/2004 | Seguin | |
| 6,869,444 B2 | 3/2005 | Gabbay | |
| 6,893,460 B2 | 5/2005 | Spenser et al. | |
| 6,908,481 B2 | 6/2005 | Cribier | |
| 7,018,406 B2 | 3/2006 | Seguin et al. | |
| 7,025,780 B2 | 4/2006 | Gabbay | |
| 7,137,184 B2 | 11/2006 | Schreck | |
| 7,160,322 B2 | 1/2007 | Gabbay | |
| 7,247,167 B2 | 7/2007 | Gabbay | |
| 7,267,686 B2 | 9/2007 | DiMatteo et al. | |
| 7,311,730 B2 | 12/2007 | Gabbay | |
| 7,374,573 B2 | 5/2008 | Gabbay | |
| 7,381,218 B2 | 6/2008 | Schreck | |
| 7,452,371 B2 | 11/2008 | Pavcnik et al. | |
| 7,510,572 B2 | 3/2009 | Gabbay | |
| 7,524,331 B2 | 4/2009 | Birdsall | |
| RE40,816 E | 6/2009 | Taylor et al. | |
| 7,585,321 B2 | 9/2009 | Cribier | |
| 7,682,390 B2 | 3/2010 | Seguin | |
| 7,731,742 B2 | 6/2010 | Schlick et al. | |
| 7,803,185 B2 | 9/2010 | Gabbay | |
| 7,846,203 B2 | 12/2010 | Cribier | |
| 7,846,204 B2 | 12/2010 | Letac et al. | |
| 7,914,569 B2 | 3/2011 | Nguyen et al. | |
| D648,854 S | 11/2011 | Braido | |
| D652,926 S | 1/2012 | Braido | |
| D652,927 S | 1/2012 | Braido et al. | |
| D653,341 S | 1/2012 | Braido et al. | |
| D653,342 S | 1/2012 | Braido et al. | |
| D653,343 S | 1/2012 | Ness et al. | |
| D654,169 S | 2/2012 | Braido | |
| D654,170 S | 2/2012 | Braido et al. | |
| D660,432 S | 5/2012 | Braido | |
| D660,433 S | 5/2012 | Braido et al. | |
| D660,967 S | 5/2012 | Braido et al. | |
| 2002/0036220 A1 | 3/2002 | Gabbay | |
| 2003/0023303 A1 | 1/2003 | Palmaz et al. | |
| 2003/0050694 A1 | 3/2003 | Yang et al. | |
| 2003/0130726 A1 | 7/2003 | Thorpe et al. | |
| 2004/0049262 A1 | 3/2004 | Obermiller et al. | |
| 2004/0093075 A1 | 5/2004 | Kuehne | |
| 2004/0210304 A1 | 10/2004 | Seguin et al. | |
| 2005/0096726 A1 | 5/2005 | Sequin et al. | |
| 2005/0137695 A1 | 6/2005 | Salahieh et al. | |
| 2005/0137697 A1 | 6/2005 | Salahieh et al. | |
| 2005/0256566 A1 | 11/2005 | Gabbay | |
| 2006/0008497 A1 | 1/2006 | Gabbay | |
| 2006/0074484 A1 | 4/2006 | Huber | |
| 2006/0106415 A1 | 5/2006 | Gabbay | |
| 2006/0122692 A1 | 6/2006 | Gilad et al. | |
| 2006/0142848 A1 | 6/2006 | Gabbay | |
| 2006/0149360 A1 | 7/2006 | Schwammenthal et al. | |
| 2006/0167468 A1 | 7/2006 | Gabbay | |
| 2006/0173532 A1 | 8/2006 | Flagle et al. | |
| 2006/0178740 A1 | 8/2006 | Stacchino et al. | |
| 2006/0206202 A1 | 9/2006 | Bonhoeffer et al. | |
| 2006/0241744 A1 | 10/2006 | Beith | |
| 2006/0241745 A1 | 10/2006 | Solem | |
| 2006/0259120 A1 | 11/2006 | Vongphakdy et al. | |
| 2006/0259137 A1 | 11/2006 | Artof et al. | |
| 2006/0265056 A1 | 11/2006 | Nguyen et al. | |
| 2006/0276813 A1 | 12/2006 | Greenberg | |
| 2007/0010876 A1 | 1/2007 | Salahieh et al. | |
| 2007/0027534 A1 | 2/2007 | Bergheim et al. | |
| 2007/0043435 A1 | 2/2007 | Seguin et al. | |
| 2007/0055358 A1 | 3/2007 | Krolik et al. | |
| 2007/0067029 A1 | 3/2007 | Gabbay | |
| 2007/0073391 A1 | 3/2007 | Bourang et al. | |
| 2007/0088431 A1 | 4/2007 | Bourang et al. | |
| 2007/0093890 A1 | 4/2007 | Eliasen et al. | |
| 2007/0100435 A1 | 5/2007 | Case et al. | |
| 2007/0112422 A1 | 5/2007 | Dehdashtian | |
| 2007/0118210 A1 | 5/2007 | Pinchuk | |
| 2007/0162100 A1 | 7/2007 | Gabbay | |
| 2007/0168013 A1 | 7/2007 | Douglas | |
| 2007/0203575 A1 | 8/2007 | Forster et al. | |
| 2007/0213813 A1 | 9/2007 | Von Segesser et al. | |
| 2007/0233228 A1 | 10/2007 | Eberhardt et al. | |
| 2007/0239271 A1 | 10/2007 | Nguyen | |
| 2007/0244545 A1 | 10/2007 | Birdsall et al. | |
| 2007/0244552 A1 | 10/2007 | Salahieh et al. | |
| 2007/0288087 A1 | 12/2007 | Fearnot et al. | |
| 2008/0021552 A1 | 1/2008 | Gabbay | |
| 2008/0039934 A1 | 2/2008 | Styrc | |
| 2008/0071369 A1* | 3/2008 | Tuval | A61F 2/2418 623/2.38 |
| 2008/0082164 A1 | 4/2008 | Friedman | |
| 2008/0097595 A1 | 4/2008 | Gabbay | |
| 2008/0114452 A1 | 5/2008 | Gabbay | |
| 2008/0125853 A1 | 5/2008 | Bailey et al. | |
| 2008/0140189 A1 | 6/2008 | Nguyen et al. | |
| 2008/0147182 A1 | 6/2008 | Righini et al. | |
| 2008/0147183 A1 | 6/2008 | Styrc | |
| 2008/0154355 A1 | 6/2008 | Benichou et al. | |
| 2008/0154356 A1 | 6/2008 | Obermiller et al. | |
| 2008/0243245 A1 | 10/2008 | Thambar et al. | |
| 2008/0255662 A1 | 10/2008 | Stacchino et al. | |
| 2008/0262602 A1 | 10/2008 | Wilk et al. | |
| 2008/0269879 A1 | 10/2008 | Sathe et al. | |
| 2009/0054975 A1 | 2/2009 | del Nido et al. | |
| 2009/0112309 A1 | 4/2009 | Jaramillo et al. | |
| 2009/0138079 A1 | 5/2009 | Tuval et al. | |
| 2010/0004740 A1 | 1/2010 | Seguin et al. | |
| 2010/0036484 A1 | 2/2010 | Hariton et al. | |
| 2010/0049306 A1 | 2/2010 | House et al. | |
| 2010/0082094 A1* | 4/2010 | Quadri | A61F 2/2412 623/1.26 |
| 2010/0087907 A1 | 4/2010 | Lattouf | |
| 2010/0131055 A1 | 5/2010 | Case et al. | |
| 2010/0168778 A1 | 7/2010 | Braido | |
| 2010/0168839 A1 | 7/2010 | Braido et al. | |
| 2010/0185277 A1 | 7/2010 | Braido et al. | |
| 2010/0191326 A1 | 7/2010 | Alkhatib | |

(56) References Cited

U.S. PATENT DOCUMENTS

| | | |
|---|---|---|
| 2010/0204781 A1 | 8/2010 | Alkhatib |
| 2010/0204785 A1 | 8/2010 | Alkhatib |
| 2010/0217382 A1 | 8/2010 | Chau et al. |
| 2010/0249911 A1 | 9/2010 | Alkhatib |
| 2010/0249923 A1 | 9/2010 | Alkhatib et al. |
| 2010/0286768 A1 | 11/2010 | Alkhatib |
| 2010/0298931 A1 | 11/2010 | Quadri et al. |
| 2011/0029072 A1 | 2/2011 | Gabbay |
| 2011/0137397 A1 | 6/2011 | Chau et al. |
| 2011/0224678 A1 | 9/2011 | Gabbay |
| 2011/0295363 A1* | 12/2011 | Girard .............. A61F 2/2412 623/1.26 |
| 2013/0150957 A1 | 6/2013 | Weber |

FOREIGN PATENT DOCUMENTS

| | | |
|---|---|---|
| DE | 202008009610 U1 | 12/2008 |
| EP | 0850607 A1 | 7/1998 |
| EP | 1000590 A1 | 5/2000 |
| EP | 1129744 A1 | 9/2001 |
| EP | 1157673 A2 | 11/2001 |
| EP | 1360942 A1 | 11/2003 |
| EP | 1584306 A1 | 10/2005 |
| EP | 1598031 A2 | 11/2005 |
| EP | 1926455 A2 | 6/2008 |
| FR | 2847800 A1 | 6/2004 |
| FR | 2850008 A1 | 7/2004 |
| WO | 9117720 A1 | 11/1991 |
| WO | 9716133 A1 | 5/1997 |
| WO | 9832412 A2 | 7/1998 |
| WO | 9913801 A1 | 3/1999 |
| WO | 01028459 A1 | 4/2001 |
| WO | 0149213 A2 | 7/2001 |
| WO | 01054625 A1 | 8/2001 |
| WO | 01056500 A2 | 8/2001 |
| WO | 01076510 A2 | 10/2001 |
| WO | 0236048 A1 | 5/2002 |
| WO | 0247575 A2 | 6/2002 |
| WO | 03047468 A1 | 6/2003 |
| WO | 06073626 A2 | 7/2006 |
| WO | 2007053243 A2 | 5/2007 |
| WO | 2007071436 A2 | 6/2007 |
| WO | 08070797 A2 | 6/2008 |
| WO | 10008548 A2 | 1/2010 |
| WO | 10008549 A1 | 1/2010 |
| WO | 10051025 A1 | 5/2010 |
| WO | 10087975 A1 | 8/2010 |
| WO | 10096176 A1 | 8/2010 |
| WO | 10098857 A1 | 9/2010 |

OTHER PUBLICATIONS

Catheter-implanted prosthetic heart valves, Knudsen, L.L., et al., The International Journal of Artificial Organs, vol. 16, No. 5 1993, pp. 253-262.
Is It Reasonable to Treat All Calcified Stenotic Aortic Valves With a Valved Stent?, 579-584, Zegdi, Rachid, MD, PhD et al., J. of the American College of Cardiology, vol. 51, No. 5, Feb. 5, 2008.
Percutaneous aortic valve replacement: resection before implantation, 836-840, Quaden, Rene et al., European J. of Cardio-thoracic Surgery, 27 (2005).
Ruiz, Carlos, "Overview of PRE-CE Mark Transcatheter Aortic Valve Technologies", Euro PCR, May 25, 2010.
Transluminal Aortic Valve Placement, Moazami, Nader, et al., ASAIO Journal, 1996; 42:M381-M385.
Transluminal Catheter Implanted Prosthetic Heart Valves, Andersen, Henning Rud, International Journal of Angiology 7:102-106 (1998).
Transluminal implantation of artificial heart valves, Andersen, H. R., et al., European Heart Journal (1992) 13, 704-708.
U.S. Appl. No. 29/375,243, filed Sep. 20, 2010.
U.S. Appl. No. 29/375,260, filed Sep. 20, 2010.

* cited by examiner

CUFF STITCHING REINFORCEMENT

CROSS-REFERENCE TO RELATED APPLICATIONS

The present application claims the benefit of the filing date of U.S. Provisional Patent Application No. 61/909,496, filed Nov. 27, 2013, the disclosure of which is hereby incorporated herein by reference.

BACKGROUND OF THE INVENTION

The present invention relates to heart valve replacement and, in particular, to collapsible prosthetic heart valves. More particularly, the present invention relates to collapsible prosthetic heart valves having improved cuff attachments.

Prosthetic heart valves that are collapsible to a relatively small circumferential size can be delivered into a patient less invasively than valves that are not collapsible. For example, a collapsible valve may be delivered into a patient via a tube-like delivery apparatus such as a catheter, a trocar, a laparoscopic instrument, or the like. This collapsibility can avoid the need for a more invasive procedure such as full open-chest, open-heart surgery.

Collapsible prosthetic heart valves typically take the form of a valve structure mounted on a stent. There are two types of stents on which the valve structures are ordinarily mounted: a self-expanding stent and a balloon-expandable stent. To place such valves into a delivery apparatus and ultimately into a patient, the valve must first be collapsed or crimped to reduce its circumferential size.

When a collapsed prosthetic valve has reached the desired implant site in the patient (e.g., at or near the annulus of the patient's heart valve that is to be replaced by the prosthetic valve), the prosthetic valve can be deployed or released from the delivery apparatus and re-expanded to full operating size. For balloon-expandable valves, this generally involves releasing the valve, assuring its proper location, and then expanding a balloon positioned within the valve stent. For self-expanding valves, on the other hand, the stent automatically expands as the sheath covering the valve is withdrawn.

SUMMARY OF THE INVENTION

In some embodiments, a prosthetic heart valve includes a collapsible and expandable stent having a proximal end, a distal end, an annulus section adjacent the proximal end and an aortic section adjacent the distal end, the stent including a plurality of struts. A cuff may be coupled to the stent so that a flat, bottom edge of the cuff lies adjacent the proximal end of the stent. A pattern of stitches may be circumferentially disposed around the flat bottom edge of the cuff, the pattern of stitches alternating between stitches sewn to the cuff only and stitches sewn to both the cuff and the stent.

In some embodiments, a prosthetic heart valve may include a collapsible and expandable stent having a proximal end, a distal end, an annulus section adjacent the proximal end and an aortic section adjacent the distal end, the stent including a plurality of struts and a plurality of commissure features. A cuff may be coupled to the stent so that a top edge of the cuff lies adjacent the plurality of commissure features and a plurality of tethers incorporated along the top edge of the cuff and coupled to the cuff only.

In some embodiments, a method of making a prosthetic heart valve may include (i) providing a collapsible and expandable stent having a proximal end, a distal end, an annulus section adjacent the proximal end and an aortic section adjacent the distal end, the stent including a plurality of struts, (ii) coupling a cuff to the stent so that a flat bottom edge of the cuff lies adjacent the proximal end of the stent, and (iii) sewing a pattern of stitches circumferentially around the flat bottom edge of the cuff, the pattern of stitches alternating between stitches sewn to the cuff only and stitches sewn to both the cuff and the stent.

BRIEF DESCRIPTION OF THE DRAWINGS

Various embodiments of the presently disclosed heart valves are disclosed herein with reference to the drawings, wherein.

Various embodiments of the present invention will now be described with reference to the appended drawings. It is to be appreciated that these drawings depict only some embodiments of the invention and are therefore not to be considered limiting of its scope.

DETAILED DESCRIPTION OF THE INVENTION

Inaccurate deployment and anchoring of a prosthetic heart valve may result in the leakage of blood between the implanted heart valve and the native valve annulus, commonly referred to as perivalvular (or "paravalvular") leakage. In aortic valves, this leakage enables blood to flow from the aorta back into the left ventricle, reducing cardiac efficiency and putting a greater strain on the heart muscle. Additionally, calcification of the aortic valve may affect performance and the interaction between the implanted valve and the calcified tissue is believed to be relevant to leakage, particularly when the native valve leaflets have not first been resected. To reduce the risk of leakage, adequate anchoring and sealing are helpful. Moreover, anatomical variations from one patient to another may affect wear and durability.

As used herein, the term "proximal," when used in connection with a prosthetic heart valve in the aortic position, refers to the end of the heart valve closest to the heart when the heart valve is implanted in a patient, whereas the term "distal," when used in connection with a prosthetic heart valve, refers to the end of the heart valve farthest from the heart when the heart valve is implanted in a patient. Also, as used herein, the word "about" is intended to mean that slight variations from absolute are included within the scope of the valve recited, for example, due to manufacturing tolerances.

Figure 1:
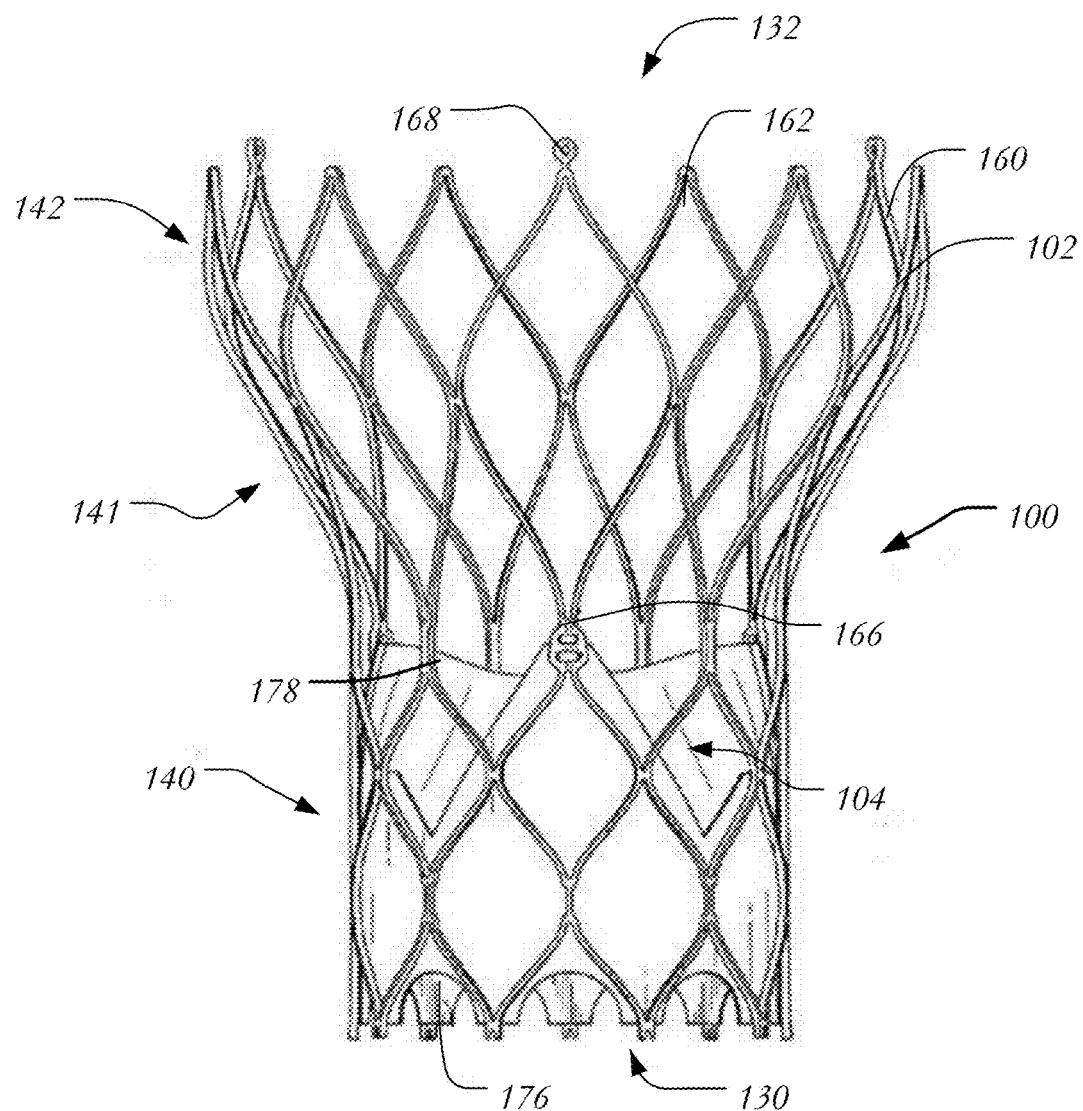
FIG. 1 is a side elevational view of a conventional prosthetic heart valve.

FIG. 1 shows a collapsible stent-supported prosthetic heart valve 100 including a stent 102 and a valve assembly 104 as is known in the art. The prosthetic heart valve 100 is designed to replace the native tricuspid valve of a patient, such as the native aortic valve. It should be noted that while the inventions herein are described predominantly in connection with their use with a prosthetic aortic valve and a stent having a shape as illustrated in FIG. 1, the valve could be a bicuspid valve, such as the mitral valve, and the stent could have different shapes, such as a flared or conical annulus section, a less-bulbous aortic section, and the like, and a differently shaped transition section.

Prosthetic heart valve 100 will be described in more detail with reference to FIG. 1. Prosthetic heart valve 100 includes expandable stent 102 which may be formed from biocompatible materials that are capable of self-expansion, such as, for example, shape memory alloys, such as the nickel-titanium alloy known as "Nitinol" or other suitable metals or polymers. Stent 102 extends from proximal or annulus end 130 to distal or aortic end 132, and includes annulus section 140 adjacent proximal end 130, transition section 141, and aortic section 142 adjacent distal end 132. Annulus section 140 has a relatively small cross-section in the expanded condition, while aortic section 142 has a relatively large cross-section in the expanded condition. Preferably, annulus section 140 is in the form of a cylinder having a substantially constant diameter along its length. Transition section 141 may taper outwardly from annulus section 140 to aortic section 142. Each of the sections of stent 102 includes a plurality of struts 160 forming cells 162 connected to one another in one or more annular rows around the stent. For example, as shown in FIG. 1, annulus section 140 may have two annular rows of complete cells 162 and aortic section 142 and transition section 141 may each have one or more annular rows of partial cells 162. Cells 162 in aortic section 142 may be larger than cells 162 in annulus section 140. The larger cells in aortic section 142 better enable prosthetic valve 100 to be positioned in the native valve annulus without the stent structure interfering with blood flow to the coronary arteries.

Stent 102 may include one or more retaining elements 168 at distal end 132 thereof, retaining elements 168 being sized and shaped to cooperate with female retaining structures (not shown) provided on a deployment device configured to deploy the prosthetic valve 100 in the native valve annulus of a patient. The engagement of retaining elements 168 with the female retaining structures on the deployment device helps maintain prosthetic heart valve 100 in assembled relationship with the deployment device, minimizes longitudinal movement of the prosthetic heart valve relative to the deployment device during unsheathing or resheathing procedures, and helps prevent rotation of the prosthetic heart valve relative to the deployment device as the deployment device is advanced to the target location and the heart valve deployed.

Prosthetic heart valve 100 includes valve assembly 104, preferably positioned in annulus section 140 of the stent 102 and secured to the stent. Valve assembly 104 includes cuff 176 and a plurality of leaflets 178 which collectively function as a one-way valve by coapting with one another. As a prosthetic aortic valve, valve 100 has three leaflets 178. However, it will be appreciated that other prosthetic heart valves with which the sealing portions of the present disclosure may be used may have a greater or lesser number of leaflets 178.

Although cuff 176 is shown in FIG. 1 as being disposed on the luminal or inner surface of annulus section 140, it is contemplated that cuff 176 may be disposed on the abluminal or outer surface of annulus section 140 or may cover all or part of either or both of the luminal and abluminal surfaces. Both cuff 176 and leaflets 178 may be wholly or partly formed of any suitable biological material or polymer such as, for example, polytetrafluoroethylene (PTFE), ultra-high molecular weight polyethylene, polyurethane, polyvinyl alcohol, silicone or combinations thereof.

Leaflets 178 may be attached along their belly portions to cells 162 of stent 102, with the commissure between adjacent leaflets 178 attached to commissure features 166 of the stent. As can be seen in FIG. 1, each commissure feature 166 may lie at the intersection of four cells 162, two of the cells being adjacent one another in the same annular row, and the other two cells being in different annular rows and lying in end-to-end relationship. Preferably, commissure features 166 are positioned entirely within annulus section 140 or at the juncture of annulus section 140 of stent 102 and transition section 141. Commissure features 166 may include one or more eyelets which facilitate the suturing of the leaflet commissure to stent 102.

Prosthetic heart valve 100 may be used to replace a native aortic valve, a surgical heart valve or a heart valve that has undergone a surgical procedure. Prosthetic heart valve 100 may be delivered to the desired site (e.g., near the native aortic annulus) using any suitable delivery device. During delivery, prosthetic heart valve 100 is disposed inside the delivery device in the collapsed condition. The delivery device may be introduced into a patient using a transfemoral, transapical, transseptal or any other percutaneous approach. Once the delivery device has reached the target site, the user may deploy prosthetic heart valve 100. Upon deployment, prosthetic heart valve 100 expands so that annulus section 140 is in secure engagement within the native aortic annulus. When prosthetic heart valve 100 is properly positioned inside the heart, it works as a one-way valve, allowing blood to flow from the left ventricle of the heart to the aorta, and preventing blood from flowing in the opposite direction.

Figure 2:
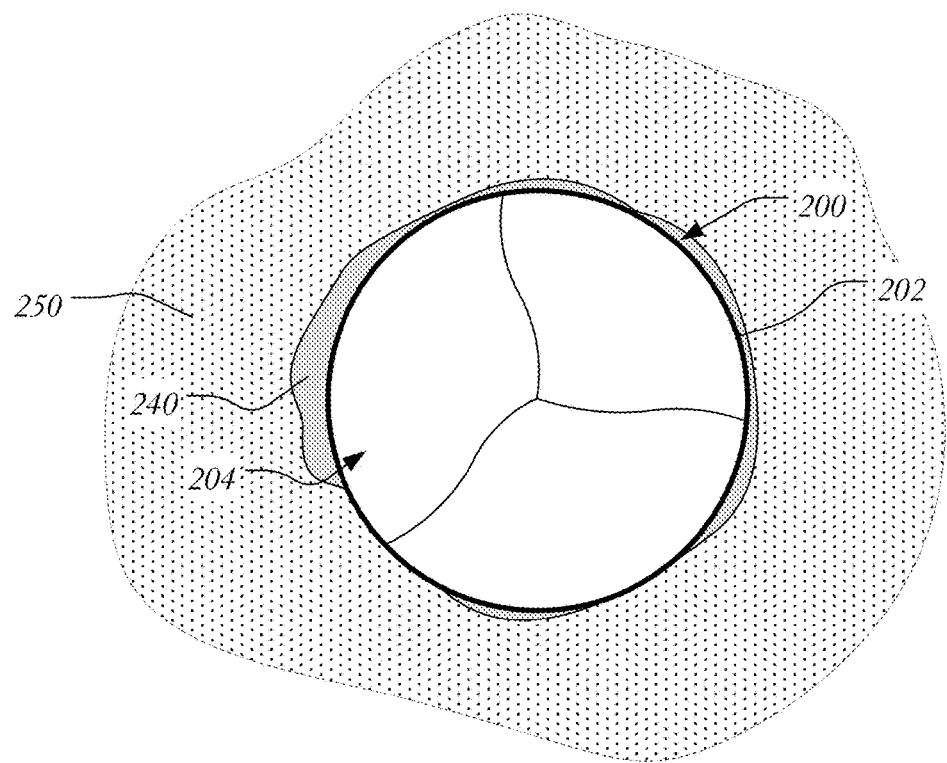
FIG. 2 is a highly schematic cross-sectional view showing another prosthetic heart valve disposed within a native valve annulus.

FIG. 2 is a highly schematic cross-sectional illustration of prosthetic heart valve 200 disposed within native valve annulus 250. As seen in the figure, stent 202 has a substantially circular cross-section which is disposed within the non-circular native valve annulus 250. At certain locations around the perimeter of heart valve 200, crescent-shaped gaps 240 form between the heart valve and native valve annulus 250. Blood flowing through these gaps and past valve assembly 204 of prosthetic heart valve 200 may be undesirable.

Figure 3A:
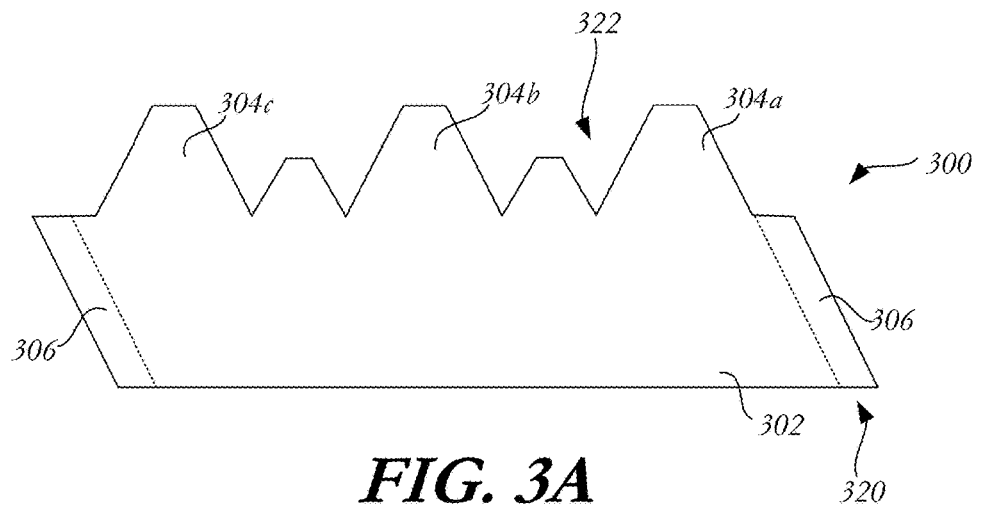
FIG. 3A is a developed view of a cuff having a series of peaks.
Figure 3B:
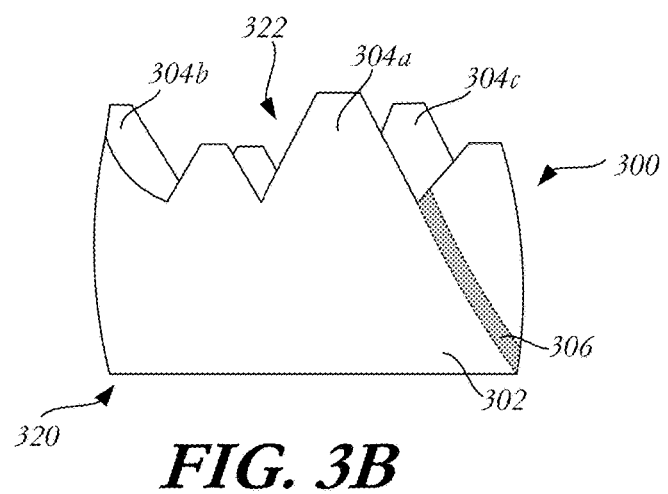
FIG. 3B is a perspective side view of the cuff of FIG. 3A after the attachment portions of the cuff have been coupled together.

FIGS. 3A and 3B illustrate the outer surface of a cuff before coupling to a stent. As shown, cuff 300 includes a generally parallelogram-shaped body 302, a series of trapezoidal or triangular peaks 304a, 304b, and 304c and a pair of attachment portions 306. It will be understood, however, that cuff 300 may be formed in various geometric shapes and that illustrated configurations are merely exemplary. Peaks 304 may be used to couple cuff 300 to a stent. Body 302 extends longitudinally from an inflow end 320 to an outflow end 322, peaks 304a, 304b, and 304c being located near outflow end 322. Attachment portions 306 are adapted to be coupled together to form cuff 300 into the wrapped or assembled configuration shown in FIG. 3B. Attachment portions 306 may overlap one another in the wrapped configuration, and may be coupled together using a suture, an adhesive or any other suitable means. Attachment portions 306 may also abut one another and couple together. Cuff 300 may be placed in the wrapped configuration before being coupled to a stent. Alternatively, cuff 300 may be first coupled to the stent after which attachment portions 306 may be coupled together.

Cuff 300 is coupled to a stent and to a number of leaflets to form a prosthetic heart valve. It will be understood that the components may be assembled using various techniques and in different orders. For example, the cuff may be coupled to the stent followed by the leaflets or the leaflets may be attached to the cuff followed by assembly of both to the stent.

Figure 4A:
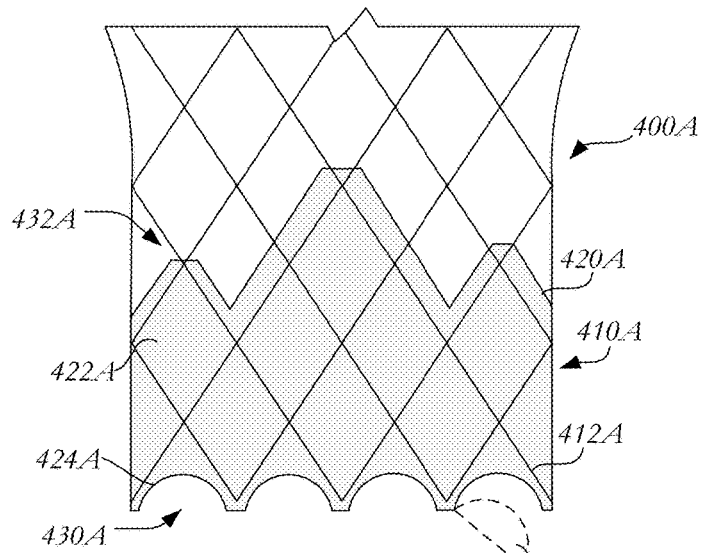
FIG. 4A is a partial schematic side view of a first variation of a prosthetic heart valve having a cuff coupled to a stent, the cuff having a plurality of cutouts.

Two variations of the final cuff-stent assembly are described below with reference to FIGS. 4A-C. In a first variation, shown in FIG. 4A, prosthetic heart valve 400A includes stent 410A formed of a plurality of struts 412A, with cuff 420A coupled to the stent. Cuff 420A includes body 422A extending between inflow end 430A and outflow end 432A.

Excess portions of cuff 420A may unduly increase the crimp profile of heart valve 400A and may also impinge on the effective orifice area (e.g., the entrance orifice through which blood flows to the valve assembly). In order to address these concerns, excess portions 440A of body 422A near inflow end 430A may be trimmed using a cutting mandrel, a die or other suitable means. A fixation device may be useful in this trimming process. One fixation device useful for this purpose is shown in U.S. Provisional Patent Application Ser. No. 61/666,174 entitled "VALVE ASSEMBLY FOR CRIMP PROFILE" filed Jun. 29, 2012, the content of which is hereby incorporated by reference herein in its entirety.

The trimming of cuff 420A may be accomplished either prior to or after the attachment of cuff 420A to stent 410A. After completion, cutouts 424A, such as the semicircular cutouts shown in FIG. 4A, are formed in cuff 420A at recurring positions along the edge near inflow end 430A. In this variation, cutouts 424A are configured to mitigate effective orifice area impingement of cuff 420A during forward flow of blood through inflow end 430A. Though cutouts 424A may reduce the crimp profile of the device, in applications where prosthetic heart valve 400A is implanted in an asymmetric annulus or in an annulus having heavily calcified regions as described above with reference to FIG. 2, cutouts 424A may not adequately seal inflow end 430A against the surrounding tissue.

Figure 4B:
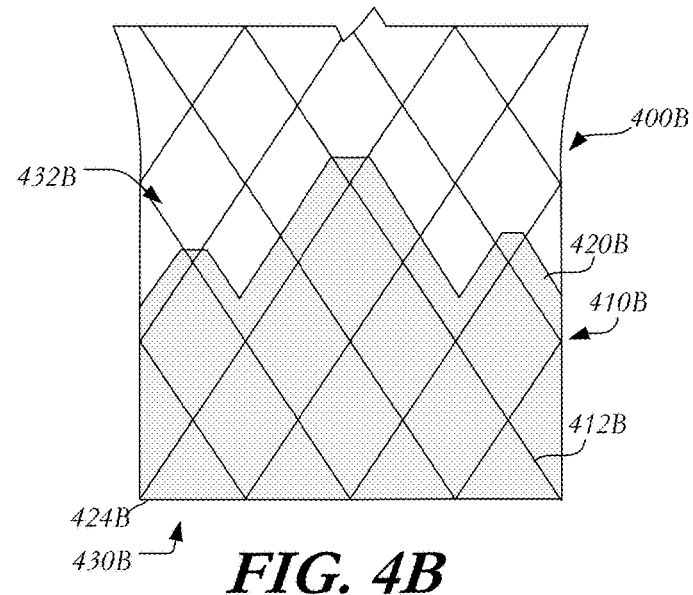
FIG. 4B is a partial schematic side view of a second variation of a prosthetic heart valve having a cuff coupled to a stent, the cuff having a substantially straight inflow edge.

In a second variation, shown in FIG. 4B, prosthetic heart valve 400B includes stent 410B formed of a plurality of struts 412B, with cuff 420B coupled to the stent. Unlike heart valve 400A, cuff 420B of heart valve 400B is not trimmed along either inflow end 430B or outflow end 432B, leaving a substantially flat edge 424B near inflow end 430B. Flat edge 424B may align with the proximal ends of struts 412 near inflow end 430B. Flat edge 424B may present some drawbacks as explained below.

Figure 4C:
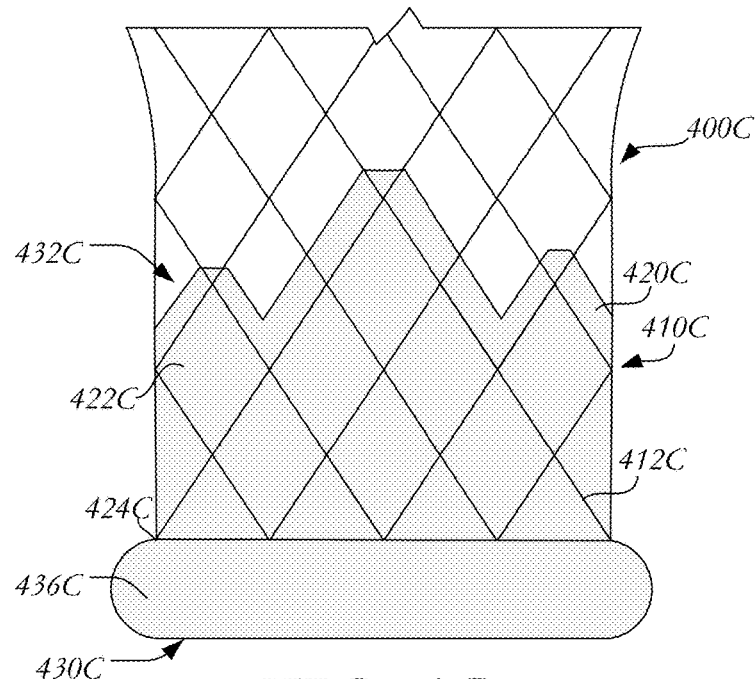
FIGS. 4C-4D are partial schematic side views of examples of cuffs having substantially straight inflow edges.
Figure 4D:
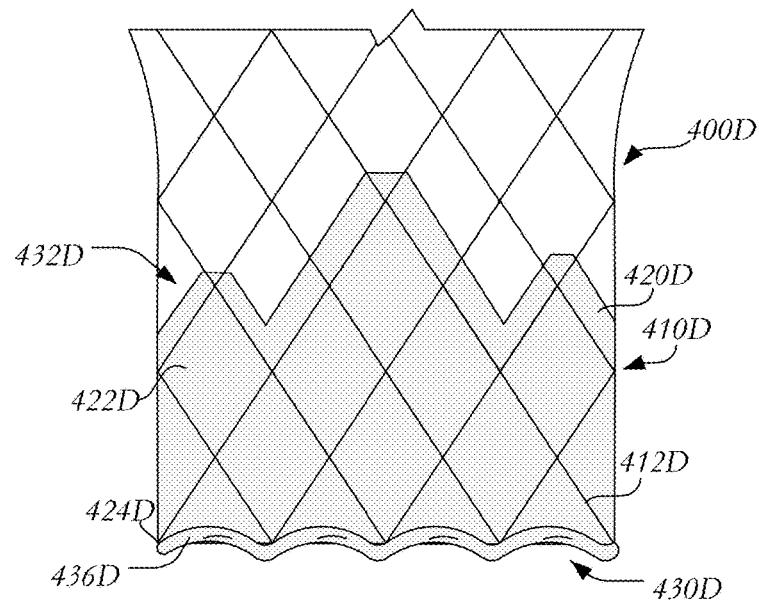

FIGS. 4C-4D are partial schematic side views of examples of cuffs having untrimmed inflow edges. In FIG. 4C, prosthetic heart valve 400C includes stent 410C formed of a plurality of struts 412C, with cuff 420C coupled to the stent. Cuff 420C is rolled on itself near inflow end 430C to create halo 436C, a ring-like portion of cuff 420C that extends past flat edge 424C. Halo 436C may be formed of the same material as cuff 420C or a different material. Additionally, halo 436C may be integrally formed with cuff 420C or may be formed of a different portion of tissue, fabric or other cuff material that is coupled to cuff 420C through adhesive, suture or other suitable techniques. In FIG. 4D, prosthetic heart valve 400D includes stent 410D formed of a plurality of struts 412D, with cuff 420D coupled to the stent. Cuff 420D is rolled on itself near inflow end 430D to create parachute 436D.

Figure 4E:
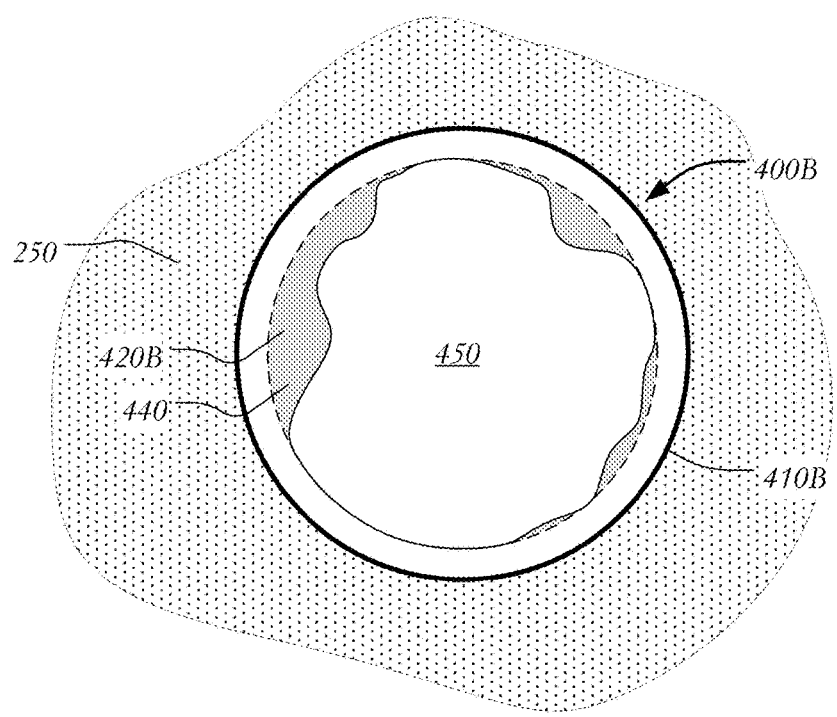
FIG. 4E is a highly schematic end view of the prosthetic heart valve of FIG. 4B disposed within a native valve annulus.

FIG. 4E is a highly schematic end view illustrating prosthetic heart valve 400B of FIG. 4B disposed within native valve annulus 250 as seen through inflow end 430B. When cutouts, such as those shown in FIG. 4A, are not formed in cuff 420B, portions of the cuff may bend inwardly during forward flow of blood. Specifically, bent portions 440 of cuff 420B that are not directly attached to struts 412B of stent 410B fold inwardly toward the central axis of prosthetic heart valve 400B, diminishing the effective orifice area 450 through which blood may flow. In some experiments, it has been found that bent portions 440 may diminish the total effective orifice area 450 by as much as about 10% to about 20%. Moreover, blood flowing through regions near bent portions 440 may be directed outside of cuff 420B as opposed to flowing through orifice area 450 of the valve assembly, leading to perivalvular leakage. Thus, bent portions 440 may cause regurgitation and other inefficiencies which reduce cardiac performance. Similar issues may also arise in examples having untrimmed portions as shown in FIGS. 4C and 4D.

Figure 5:
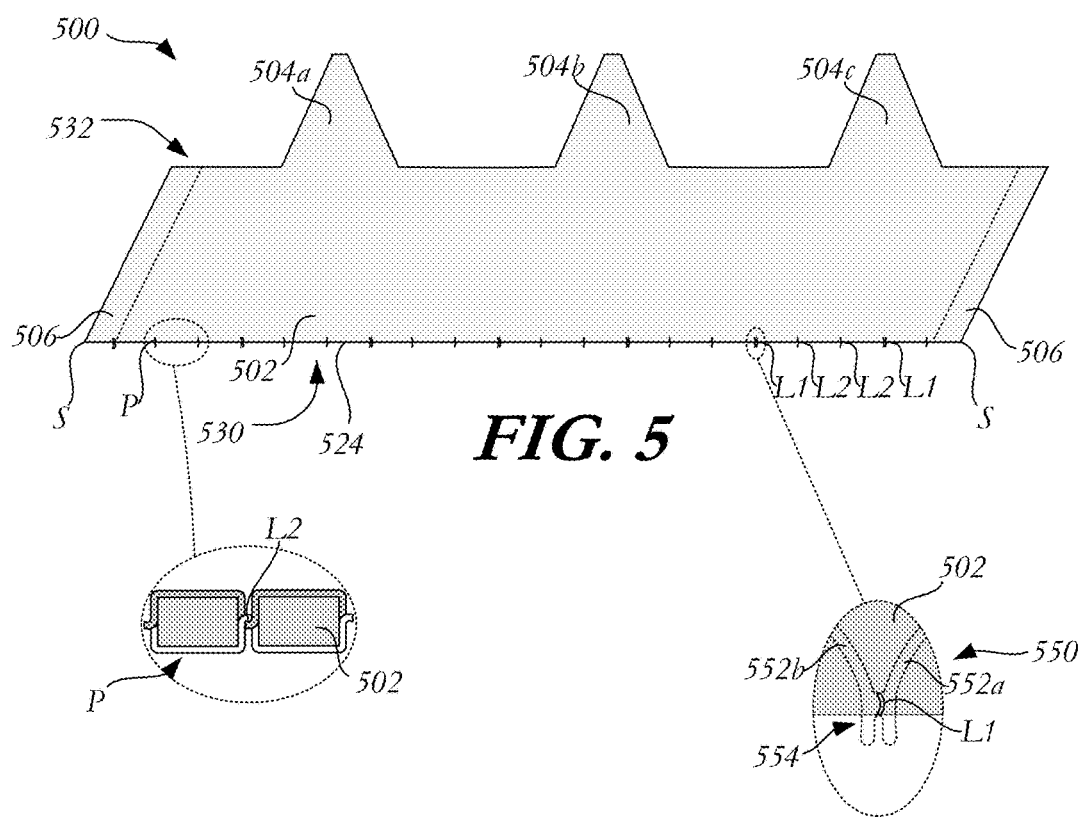
FIG. 5 is a developed view of a cuff having stitches attached near the inflow end.

Several techniques will be described to reduce the formation of bent portions in the cuff and to avoid constriction of the effective orifice area through the prosthetic heart valve. FIG. 5 illustrates one such technique, which uses stitches to reduce bent portions of the cuff. For the sake of illustration, cuff 500 is shown flat, as if stretched out and only a portion of a stent is shown in detail. Cuff 500 includes body 502, a series of large peaks 504a, 504b, and 504c projecting from one edge of body 502, and a pair of attachment portions 506, one on each longitudinal end of body 502. To minimize the formation of bent portions of the cuff during use, as shown in FIG. 4E, a stitching technique may be applied along flat edge 524 of body 502 near inflow end 530. In one example, a stitch pattern P may be disposed along flat edge 524 to eliminate or minimize bending of the cuff.

An enlarged detailed view of FIG. 5 is shown of body 502 as well as portions of select struts 552a, 552b (shown in broken lines) to which body 502 will be attached. For the sake of clarity, the remaining portions of the stent are not shown. As shown in the detailed view, when two struts 552a and 552b join at the inflow end of stent 550, a horseshoe 554 is formed. Stitch pattern P may include a first horseshoe locking stitch L1 anchored at each horseshoe 554. Between adjacent horseshoe locking stitches L1, stitch pattern P may include additional locking stitches L2 sewn to cuff 500 only, as shown in the enlarged detailed view in FIG. 5. Each locking stitch may include two threads that entwine together at the cuff. Although FIG. 5 shows two such locking stitches L2 between adjacent horseshoe locking stitches L1, cuff 500 may include a greater or lesser number of locking stitches L2 as desired. To get from one horseshoe locking stitches L1 to another, any type of stitch may be used though locking stitches L2 are shown which minimize bulkiness. Thus, stitch pattern P may begin at the attachment portion 506 at one end of cuff 500 and form a recurring pattern of a single horseshoe locking stitch L1 coupling cuff 500 to a horseshoe 554 of stent 550 and two additional locking stitches L2 sewn to the cuff only. Stitch pattern P may begin and end in the attachment portions 506 so that the beginning and end knots are hidden when the cuff 500 is fully attached to stent 550 and the attachment portions are joined together.

Such a stitching technique allows the prosthetic heart valve to achieve a small crimp profile when collapsed for delivery, while securing each section of cuff 500 to stent 550 and minimizing bending of cuff tissue into the flow area. Additionally, it is common to create a stent 550 having a fully-expanded diameter that is greater than the diameter the stent will have in use. Thus, stitch pattern P may have the added benefit of ensuring optimal valve performance by limiting cuff 500 from over-expanding outside the optimal use range. Finally, stitch pattern P may reduce or eliminate the inward bending of cuff 500 at inflow end 530, thereby improving sealing by providing a larger landing zone and maintaining the effective orifice area through which blood may flow, while at the same time increasing the landing area along which the native valve annulus may be positioned relative to the prosthetic heart valve allowing easier placement by the physician. Larger landing areas may provide more forgiving placement accuracy. Stitch pattern P may provide these benefits while not unduly increasing the crimp profile of the prosthetic heart valve.

Figure 6:
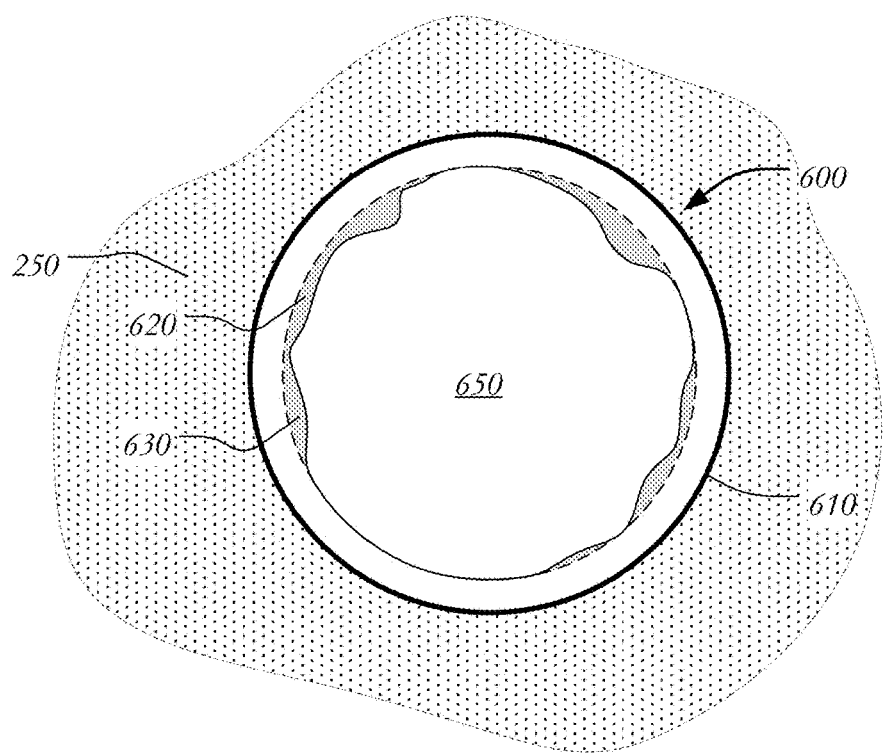
FIG. 6 is a highly schematic end view of the prosthetic heart valve of FIG. 5 disposed within a native valve annulus.

FIG. 6 is a highly schematic end view illustrating prosthetic heart valve 600 disposed within native valve annulus 250. Prosthetic heart valve 600 includes cuff 620 coupled to stent 610. A stitching technique as described with reference to FIG. 5 has been applied to cuff 620. Specifically, stitch pattern P has been applied along the circumference of cuff 620 at its inflow end. Because of the stitching technique, bent portions 630 of the cuff are reduced, leading to a larger effective orifice area 650 through which blood may flow and more adequate sealing with surrounding tissue at the inflow end of prosthetic heart valve 600.

Figure 7A:
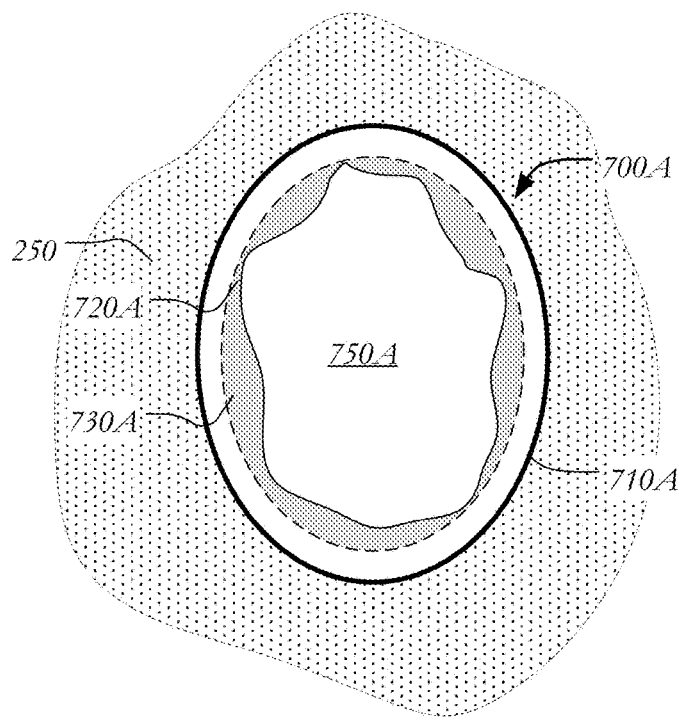
FIGS. 7A and 7B are a highly schematic end views of a prosthetic heart valve disposed within a generally elliptical native valve annulus, the prosthetic heart valve having and not having cuff inflow end stitches, respectively.
Figure 7B:
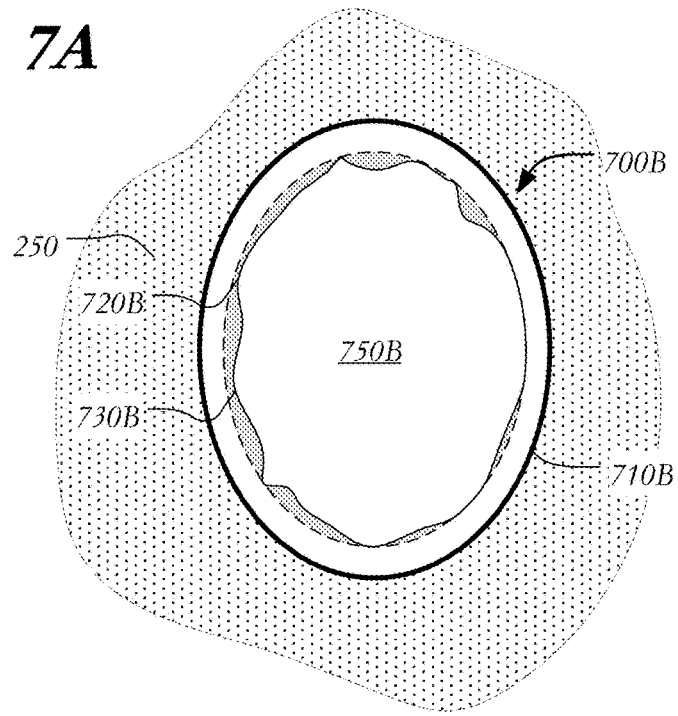

The advantages of the stitching technique described above will also be readily seen when a prosthetic heart valve is implanted in an irregularly-shaped or elliptical native valve annulus. FIGS. 7A and 7B are highly schematic cross-sectional illustrations of prosthetic heart valves 700A and 700B disposed within an elliptical native valve annulus 250. Prosthetic heart valve 700A includes cuff 720A coupled to stent 710A, but does not employ the stitching technique described above. When prosthetic heart valve 700A is deployed in elliptical native annulus 250, bicuspid or mitral valves and subjected to blood flow, bent portions 730A are formed, reducing the effective orifice area 750A through which blood may flow. Prosthetic heart valve 700B is similar to heart valve 700A, and includes cuff 720B coupled to stent 710B. However, in prosthetic heart valve 700B, the stitching technique described above with reference to FIG. 5 has been applied to cuff 720B. When prosthetic heart valve 700B is deployed in elliptical native annulus 250 and subjected to blood flow, the formation of bent portions 730B is minimized, leading to great apposition of cuff 720B to stent 710B, a larger effective orifice area 750B through which blood may flow, and more adequate sealing with surrounding tissue at the inflow end of the prosthetic heart valve.

Figure 8:
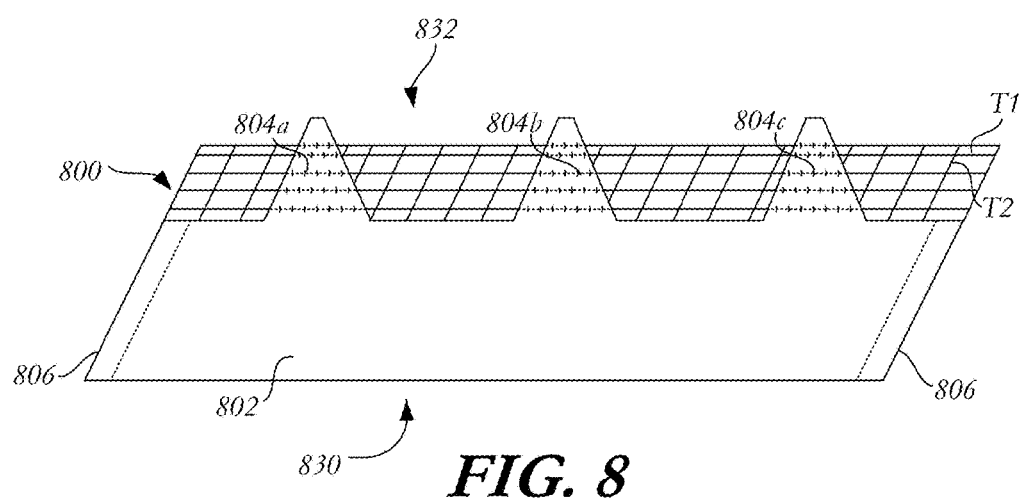
FIG. 8 is a developed view of a cuff having stitches attached near the outflow edge.

FIG. 8 illustrates another example of a cuff for promoting the sealing of the prosthetic heart valve against surrounding tissue and maximizing the effective orifice area through which blood may flow through the prosthetic heart valve. Cuff 800 includes body 802, a series of peaks 804a, 804b, and 804c at the outflow end 832 of body 802, and a pair of attachment portions 806, one on each longitudinal end of body 802. Body 802 extends between inflow end 830 and outflow end 832. To minimize the formation of bent portions of the cuff during use, as shown in FIG. 4E, a tethering technique may be applied near outflow end 832 of cuff 800. In one example, a plurality of horizontal tethers T1 may be used to attach peaks 804a, 804b, and 804c to one another. Though cuff 800 is shown in the flat configuration, it will be understood that when the cuff is in the wrapped configuration, one set of tethers T1 attach peak 804a to peak 804c. Vertical tethers T2 attach the horizontal tethers T1 to one another, creating a net-like structure or web. By adding tethers T1 and T2 near outflow end 832 of cuff 800, the landing zone of the prosthetic heart valve is increased without unduly increasing its crimp profile. In general, a longer landing zone corresponds to better sealing. In some variations, instead of using separate horizontal tethers T1 and vertical tethers T2, a preformed webbing, netting or mesh may be attached to the top of body 802 or peaks 804a, 804b, 804c to increase the landing zone in a similar manner.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

In some embodiments, a prosthetic heart valve, includes a collapsible and expandable stent having a proximal end, a distal end, an annulus section adjacent the proximal end and an aortic section adjacent the distal end, the stent including a plurality of struts. A cuff may be coupled to the stent so that a flat, bottom edge of the cuff lies adjacent the proximal end of the stent. A pattern of stitches may be circumferentially disposed around the flat bottom edge of the cuff, the pattern of stitches alternating between stitches sewn to the cuff only and stitches sewn to both the cuff and the stent.

In some examples, the pattern of stitches may include a plurality of locking stitches. The pattern of stitches may include a recurring pattern comprised of a first type of stitch and a second type of stitch. The first type of stitch may be a locking stitch sewn to the cuff only. The second type of stitch may be a locking stitch sewn to the cuff and at least a portion of the stent. The recurring pattern may include two adjacent stitches of the first type followed by a single stitch of the second type. The plurality of struts may form horseshoe-shaped portions at the proximal end of the stent, and the pattern of stitches may couple the cuff to the horseshoe-shaped portions. The pattern of stitches may include locking stitches sewn only to the cuff between the horseshoe-shaped portions.

In some embodiments, a prosthetic heart valve may include a collapsible and expandable stent having a proximal end, a distal end, an annulus section adjacent the proximal end and an aortic section adjacent the distal end, the stent including a plurality of struts and a plurality of commissure features. A cuff may be coupled to the stent so that a top edge of the cuff lies adjacent the plurality of commissure features and a plurality of tethers incorporated along the top edge of the cuff and coupled to the cuff only.

In some examples, the stent may include a plurality of commissure features and the top edge of the cuff includes a plurality of peaks coupled to the commissure features. The plurality of tethers may include at least one vertical tether and at least one horizontal tether. Adjacent ones of the plurality of peaks may be coupled to one another via the at least one horizontal tether. The at least one vertical tether may be coupled to the at least one horizontal tether. The at least one vertical tether may include multiple vertical tethers disposed between the plurality of peaks.

In other embodiments, a method of making a prosthetic heart valve may include (i) providing a collapsible and expandable stent having a proximal end, a distal end, an annulus section adjacent the proximal end and an aortic section adjacent the distal end, the stent including a plurality of struts, (ii) coupling a cuff to the stent so that a flat bottom edge of the cuff lies adjacent the proximal end of the stent, and (iii) sewing a pattern of stitches circumferentially around the flat bottom edge of the cuff, the pattern of stitches alternating between stitches sewn to the cuff only and stitches sewn to both the cuff and the stent.

In some examples, sewing a pattern of stitches may include forming a plurality of locking stitches. Sewing a pattern of stitches may include sewing a recurring pattern comprised of a first type of stitch and a second type of stitch. Sewing a pattern of stitches may include sewing a first type of stitch that is a locking stitch sewn to the cuff only. Sewing a pattern of stitches may include sewing a second type of stitch that is a locking stitch sewn to the cuff and at least a portion of the stent. The plurality of struts may form horseshoe-shaped portions at the proximal end of the stent, and sewing a pattern of stitches may include sewing the cuff to the horseshoe-shaped portions.

It will be appreciated that the various dependent claims and the features set forth therein can be combined in different ways than presented in the initial claims. It will also be appreciated that the features described in connection with individual embodiments may be shared with others of the described embodiments.

The invention claimed is:

1. A prosthetic heart valve, comprising:
   a collapsible and expandable stent having an inflow end at a proximal end, an outflow end at a distal end, an annulus section adjacent the inflow end and an aortic section adjacent the outflow end, the stent including a plurality of struts forming a plurality of cells disposed in rows;
   a cuff coupled to the stent so that a flat bottom edge of the cuff lies adjacent the inflow end of the stent, the cuff fully covering each cell of a proximal-most row of cells closest to the inflow end of the stent; and
   a pattern of stitches circumferentially disposed around the flat bottom edge of the cuff, the pattern of stitches alternating between stitches of a first type having a first shape and being sewn to the cuff only and stitches of a second type having a second shape different from the first shape and being sewn to both the cuff and the stent.

2. The prosthetic heart valve of claim 1, wherein the pattern of stitches includes a plurality of locking stitches.

3. The prosthetic heart valve of claim 1, wherein the first type of stitch is a locking stitch sewn to the cuff only.

4. The prosthetic heart valve of claim 1, wherein the second type of stitch is a locking stitch sewn to the cuff and to at least a portion of the stent.

5. The prosthetic heart valve of claim 1, wherein the pattern includes two adjacent stitches of the first type followed by a single stitch of the second type.

6. The prosthetic heart valve of claim 1, wherein the plurality of struts form horseshoe-shaped ends at the inflow end of the stent, and the pattern of stitches couples the cuff to the horseshoe-shaped ends.

7. The prosthetic heart valve of claim 6, wherein the pattern of stitches includes locking stitches sewn only to the cuff between the horseshoe-shaped ends.

8. The prosthetic heart valve of claim 1, wherein each of the plurality of cells has apices, and the stitches sewn to both the cuff and the stent are coupled to proximal-most ones of the apices.

9. The prosthetic heart valve of claim 1, wherein the stitches sewn to both the cuff and the stent are coupled to a single location of each of a number of the plurality of cells.

10. A method of making a prosthetic heart valve, comprising:
    providing a collapsible and expandable stent having an inflow end at a proximal end, an outflow end at a distal end, an annulus section adjacent the inflow end and an aortic section adjacent the outflow end, the stent including a plurality of struts forming a plurality of cells disposed in rows;
    coupling a cuff to the stent so that a flat bottom edge of the cuff lies adjacent the inflow end of the stent so that the cuff fully covers each cell of a proximal-most row of cells closest to the inflow end of the stent; and
    sewing a pattern of stitches circumferentially around the flat bottom edge of the cuff, the pattern of stitches alternating between stitches of a first type having a first shape and sewn to the cuff only and stitches of a second type having a second shape different from the first shape and sewn to both the cuff and the stent.

11. The method of claim 10, wherein sewing the pattern of stitches comprises forming a plurality of locking stitches.

12. The method of claim 10, wherein sewing a pattern of stitches comprises sewing a recurring pattern comprised of the first type of stitch and the second type of stitch.

13. The method of claim 10, wherein sewing a pattern of stitches comprises sewing a first type of stitch that is a locking stitch sewn to the cuff only.

* * * * *